US009668813B2

(12) United States Patent
Horvath et al.

(10) Patent No.: US 9,668,813 B2
(45) Date of Patent: Jun. 6, 2017

(54) OUTER COVER OF A PEN NEEDLE FOR A DRUG DELIVERY PEN

(71) Applicant: Becton, Dickinson and Company, Franklin Lakes, NJ (US)

(72) Inventors: Joshua D. Horvath, Sparta, NJ (US); Deirdre Collins, New York, NY (US); Charles G. Hwang, Wellesley, MA (US); Paul Upham, Jersey City, NJ (US); Sean Sullivan, Jersey City, NJ (US); Ed Langill, Oakville (CA)

(73) Assignee: Becton, Dickinson and Company, Franklin Lakes, NJ (US)

( * ) Notice: Subject to any disclaimer, the term of this patent is extended or adjusted under 35 U.S.C. 154(b) by 129 days.

(21) Appl. No.: 14/458,797

(22) Filed: Aug. 13, 2014

(65) Prior Publication Data
US 2014/0350487 A1 Nov. 27, 2014

Related U.S. Application Data

(62) Division of application No. 12/563,092, filed on Sep. 18, 2009, now abandoned.

(51) Int. Cl.
*B65D 85/20* (2006.01)
*A61B 19/02* (2006.01)
(Continued)

(52) U.S. Cl.
CPC ...... *A61B 19/0256* (2013.01); *A61B 17/3494* (2013.01); *A61B 50/20* (2016.02);
(Continued)

(58) Field of Classification Search
USPC .................. 206/363, 364, 365, 366, 370
See application file for complete search history.

(56) References Cited

U.S. PATENT DOCUMENTS 2,467,678 A   4/1949   Lockhart
2,645,339 A   7/1953   Toy
(Continued)

FOREIGN PATENT DOCUMENTS

FR   2 671 730 A1   7/1992
GB   2 437 923      11/2007
(Continued)

OTHER PUBLICATIONS

English Translation of Official Notice of Rejection mailed May 20, 2014, Issued in JP Patent Application No. 2010-210948, 5 pages.

*Primary Examiner* — Jacob K Ackun
(74) *Attorney, Agent, or Firm* — Dickinson Wright PLLC

(57) ABSTRACT

A connecting member removably connects a plurality of pen needles together, thereby providing a convenient way for a patient to carry multiple pen needles. The connecting member may be integrally formed with the outer cover of the pen needle or may be a separate member that removably receives the pen needle. An outer cover of a pen needle is provided with gripping means to facilitate gripping and handling of the outer cover. A lid connects to the outer cover to seal the outer cover. The lid also has gripping means to facilitate gripping and handling the lid. A cap is provided that has a first opening for receiving a first end of the outer cover and a second opening for receiving a second end of the outer cover.

6 Claims, 22 Drawing Sheets

(51) Int. Cl.
*A61M 5/00* (2006.01)
*A61M 5/32* (2006.01)
*A61B 17/34* (2006.01)
*A61B 50/20* (2016.01)

(52) U.S. Cl.
CPC .......... *A61M 5/002* (2013.01); *A61M 5/3202* (2013.01); *A61M 5/3213* (2013.01); *A61M 5/3205* (2013.01); *A61M 2005/3215* (2013.01)

(56) References Cited

U.S. PATENT DOCUMENTS

| | | | |
|---|---|---|---|
| 2,726,759 A * | 12/1955 | Fleming | A61M 5/002 206/366 |
| 3,114,455 A | 12/1963 | Stagg et al. | |
| 3,149,717 A | 9/1964 | Castelli | |
| 3,245,567 A | 4/1966 | Knight | |
| 3,329,146 A | 7/1967 | Waldman, Jr. | |
| 3,333,682 A | 8/1967 | Burke | |
| 3,434,473 A | 3/1969 | Smith | |
| 3,934,722 A | 1/1976 | Goldberg | |
| 4,892,525 A | 1/1990 | Hermann et al. | |
| 5,336,197 A | 8/1994 | Kuracina et al. | |
| 5,381,916 A | 1/1995 | Strawder | |
| 5,439,453 A | 8/1995 | Kashanchi | |
| 5,545,145 A * | 8/1996 | Clinton | A61M 5/002 206/366 |
| 5,873,462 A | 2/1999 | Nguyen et al. | |
| 5,876,381 A | 3/1999 | Pond et al. | |
| 6,305,541 B1 | 10/2001 | Tanner et al. | |
| 6,346,094 B2 * | 2/2002 | West | 206/365 |
| 6,382,417 B2 | 5/2002 | Kanner et al. | |
| 6,783,003 B2 | 8/2004 | Simm et al. | |
| 6,923,319 B1 * | 8/2005 | Erickson | A61M 5/008 206/366 |
| 7,134,550 B2 | 11/2006 | Groth | |
| 7,874,426 B2 | 1/2011 | Castellani | |
| 8,413,811 B1 | 4/2013 | Arendt | |
| 9,216,253 B2 * | 12/2015 | Spool | A61M 5/002 |
| 2003/0015444 A1 | 1/2003 | Molin et al. | |
| 2003/0222228 A1 | 12/2003 | Chen Fu et al. | |
| 2004/0000550 A1 | 1/2004 | Taccolini et al. | |
| 2004/0178098 A1 | 9/2004 | Swenson et al. | |
| 2006/0032769 A1 | 2/2006 | Erickson et al. | |
| 2006/0229562 A1 | 10/2006 | Marsh et al. | |

FOREIGN PATENT DOCUMENTS

| | | |
|---|---|---|
| JP | 2000-262616 | 9/2000 |
| JP | 2001-286562 | 10/2001 |
| WO | WO 00/54691 | 9/2000 |
| WO | WO 02/11797 A1 | 2/2002 |

\* cited by examiner

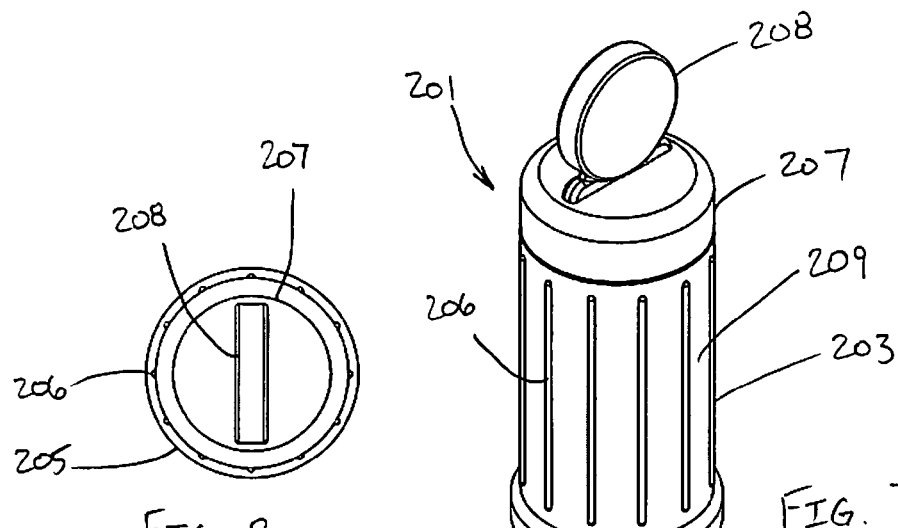
FIG. 8
FIG. 7
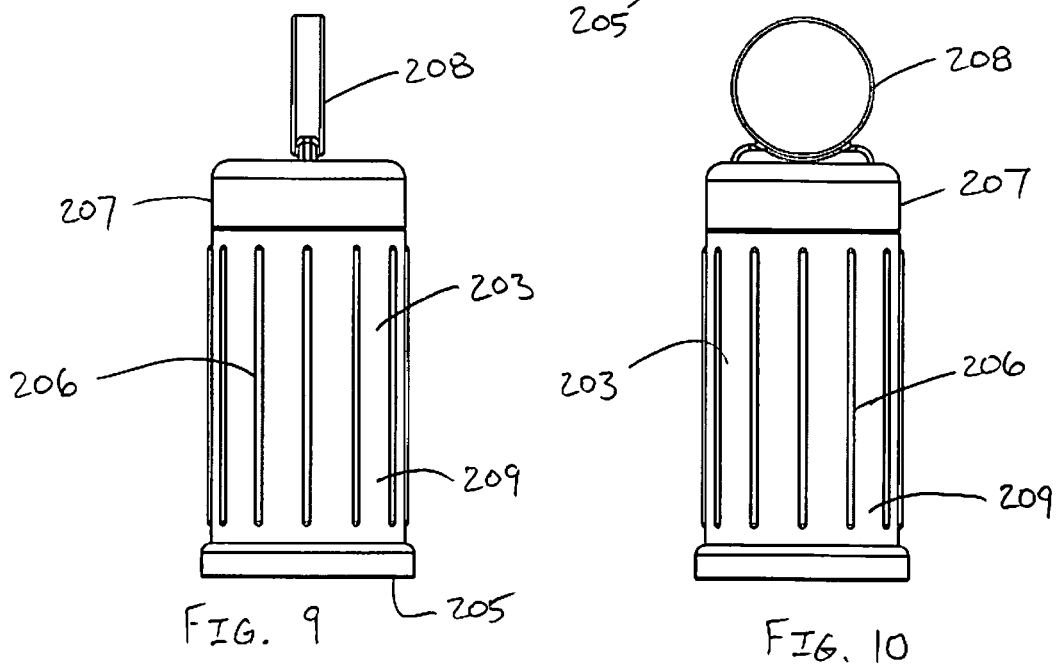
FIG. 9
FIG. 10
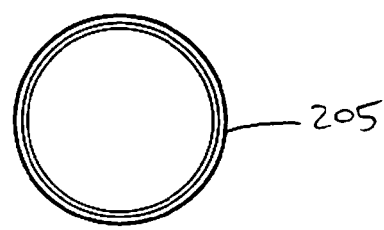
FIG. 11

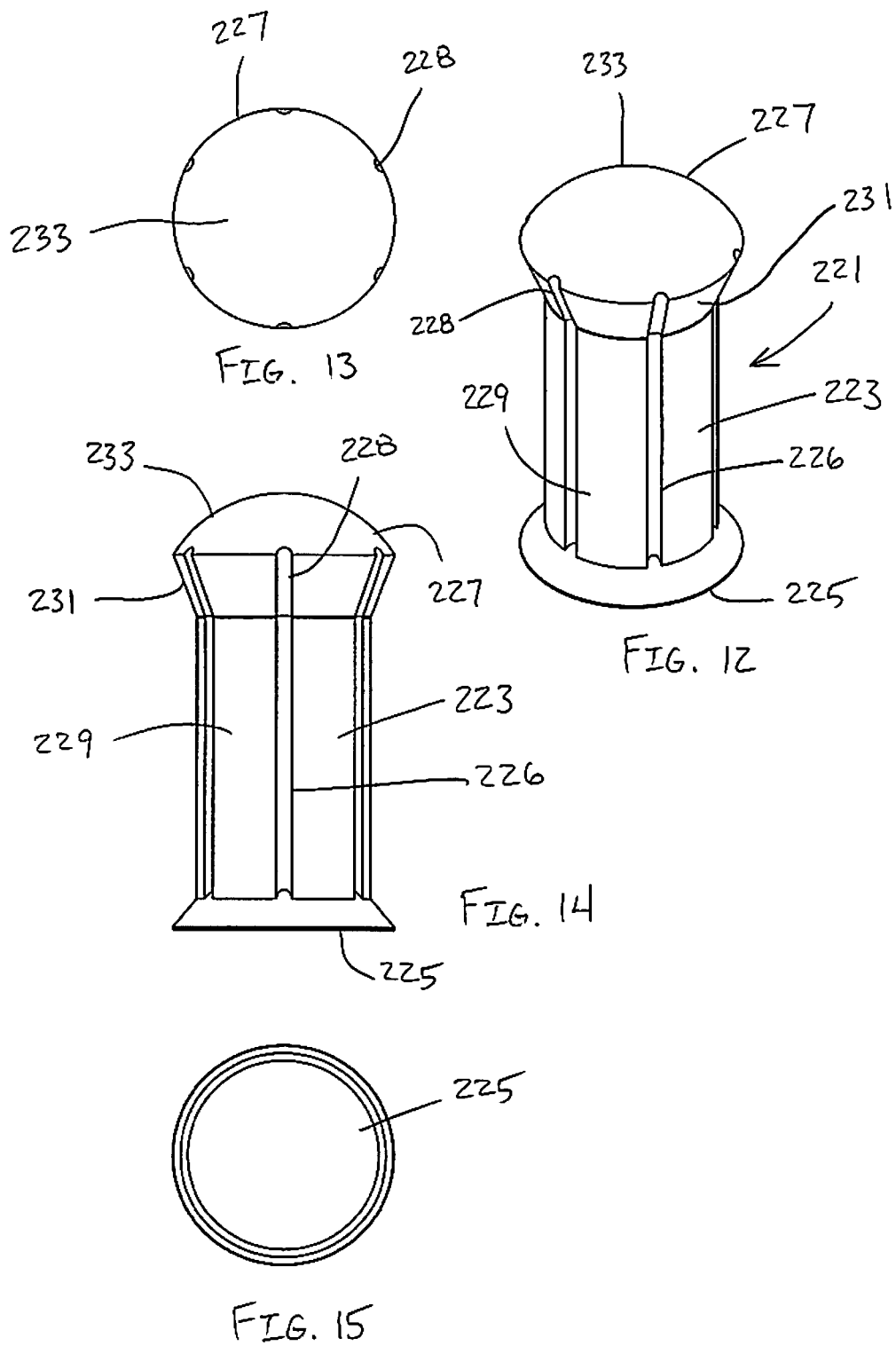

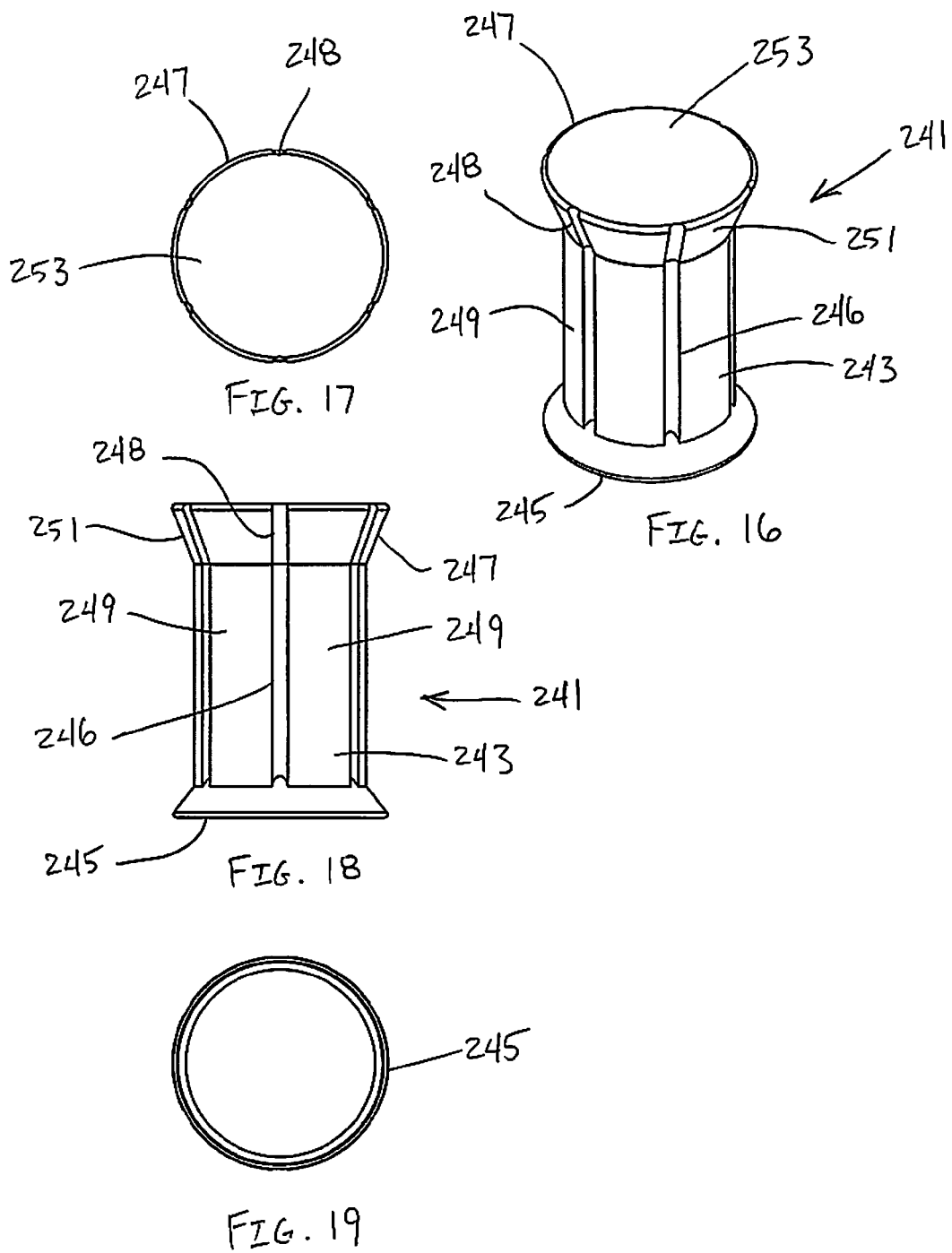

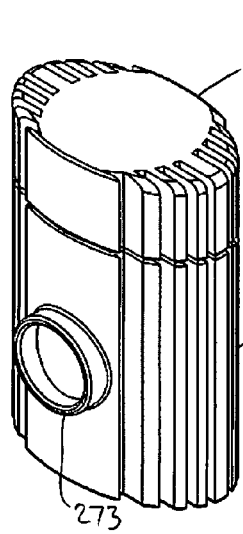
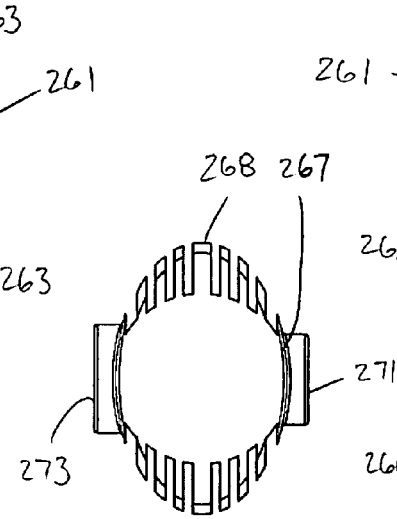
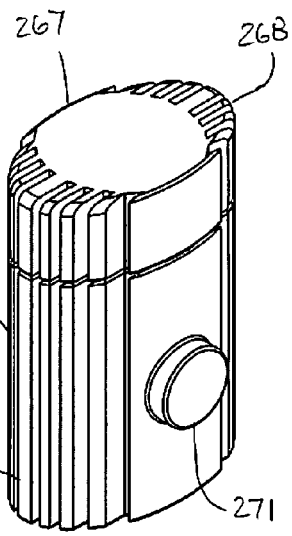
FIG. 21    FIG. 22    FIG. 20
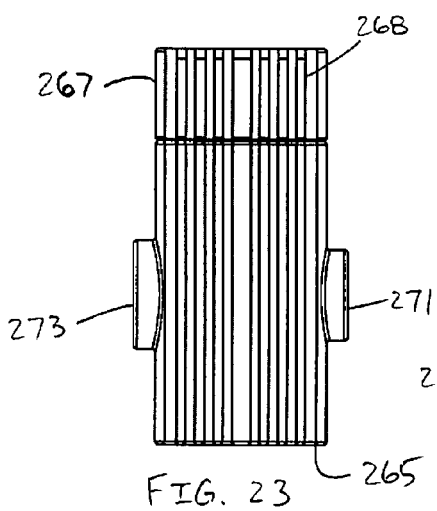
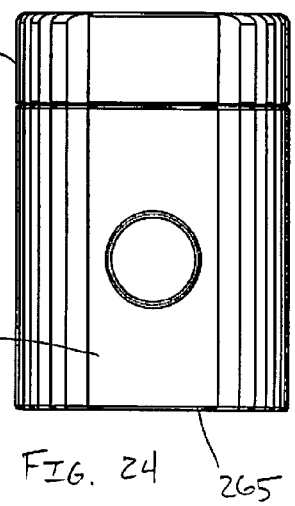
FIG. 23    FIG. 24
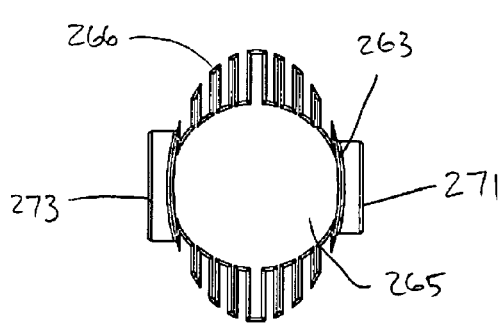
FIG. 25

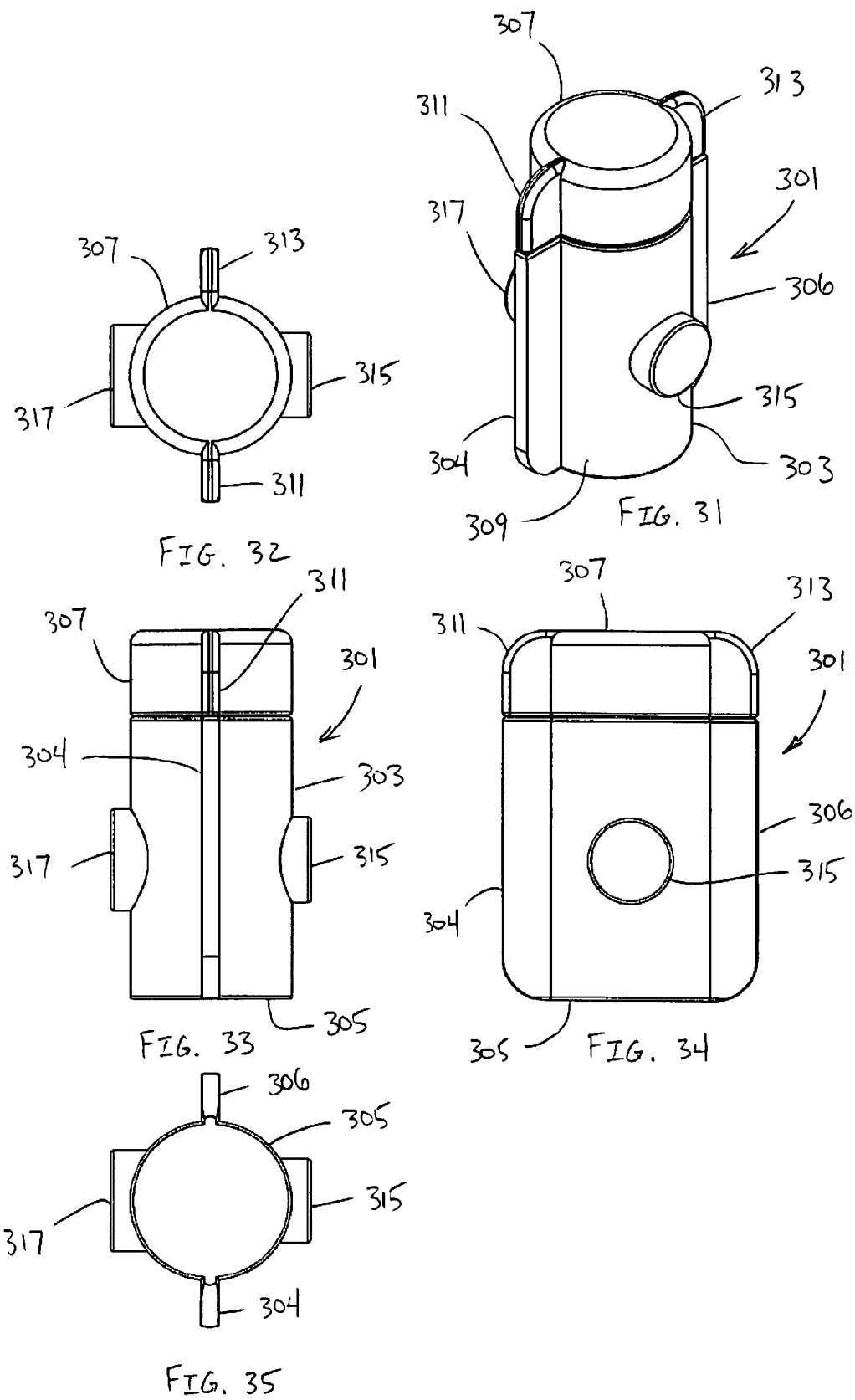

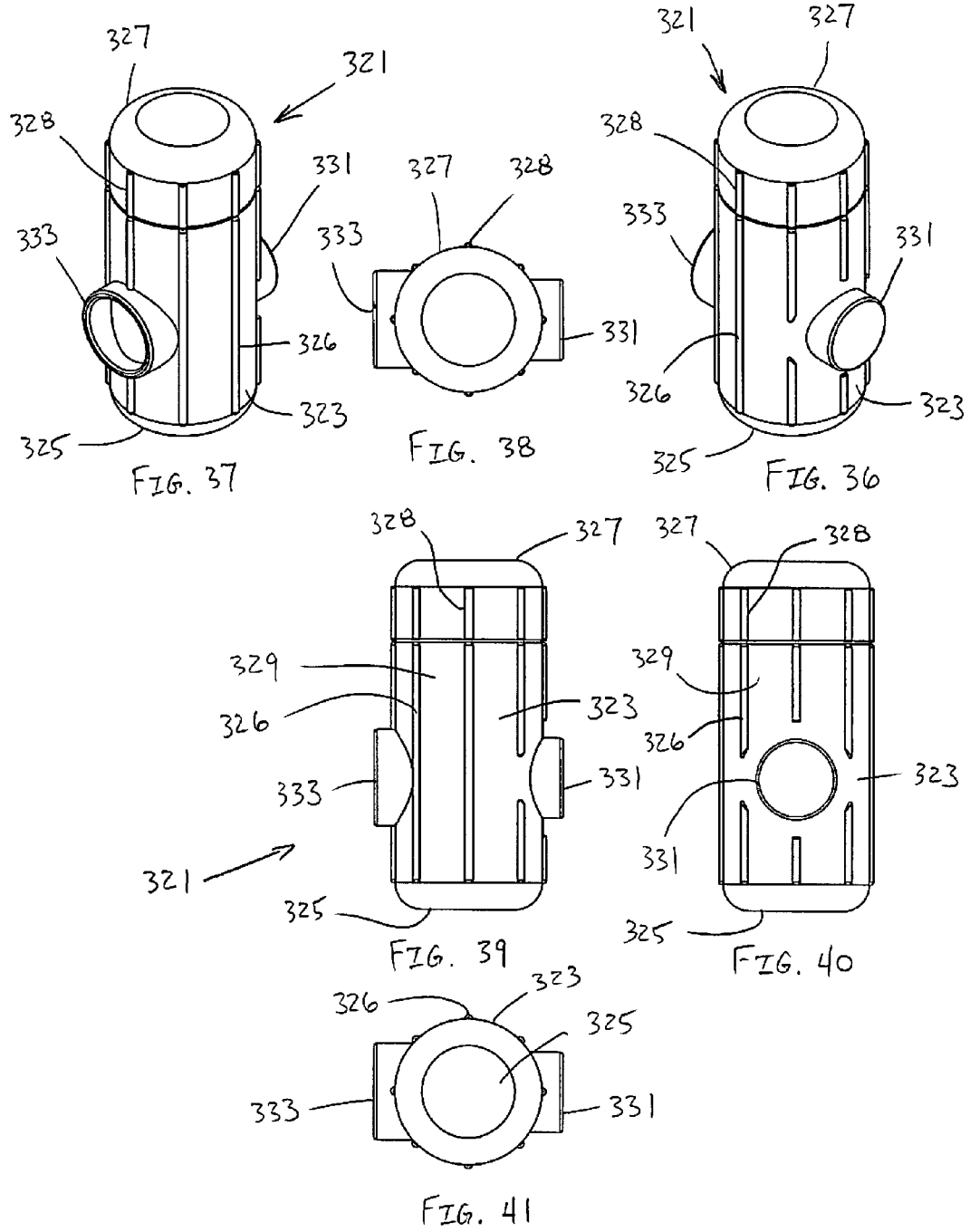

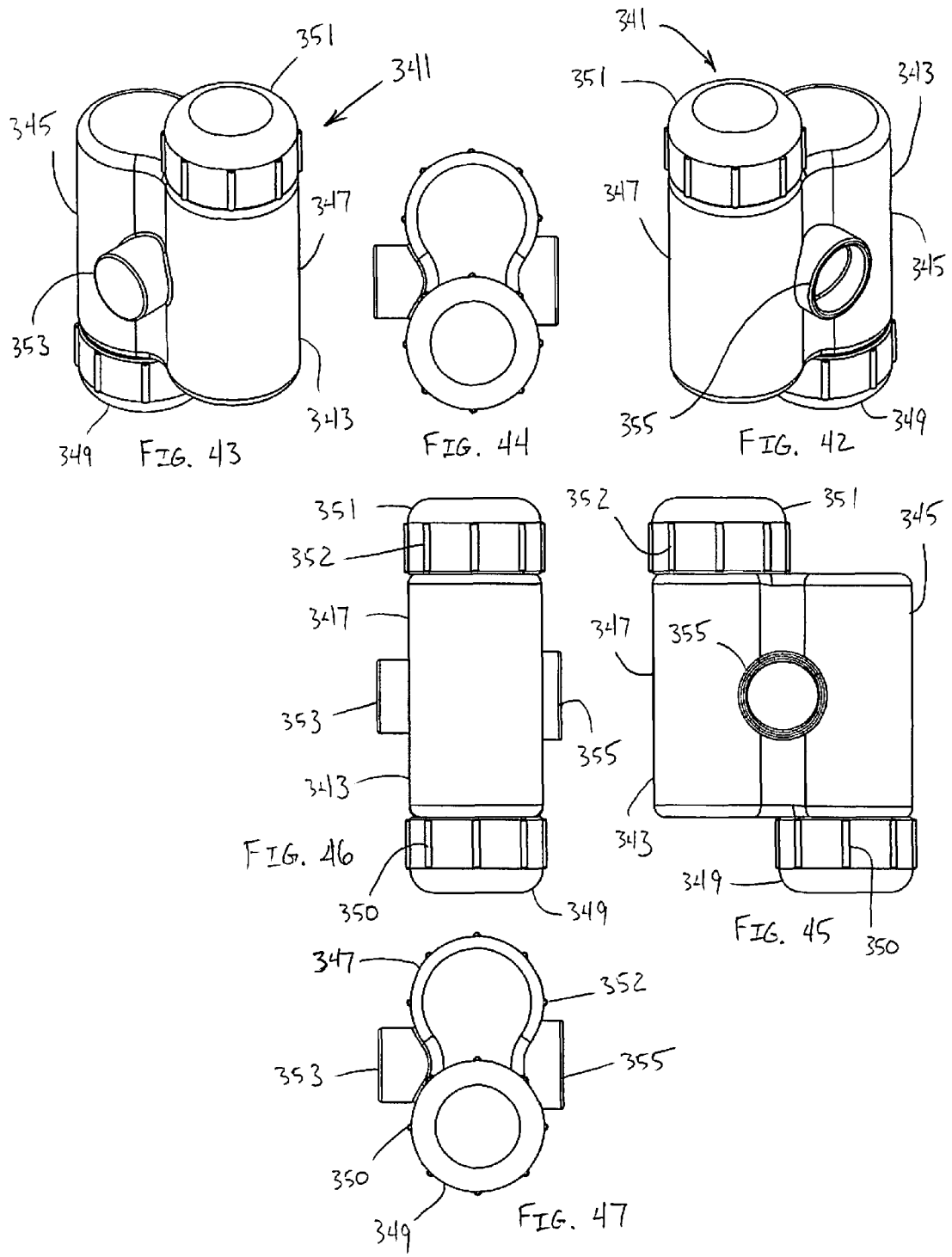

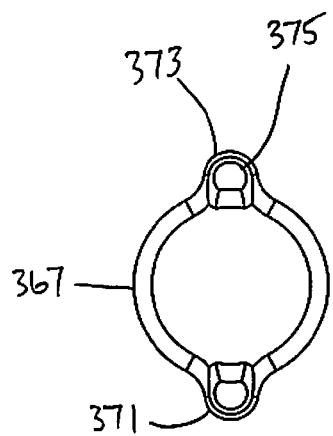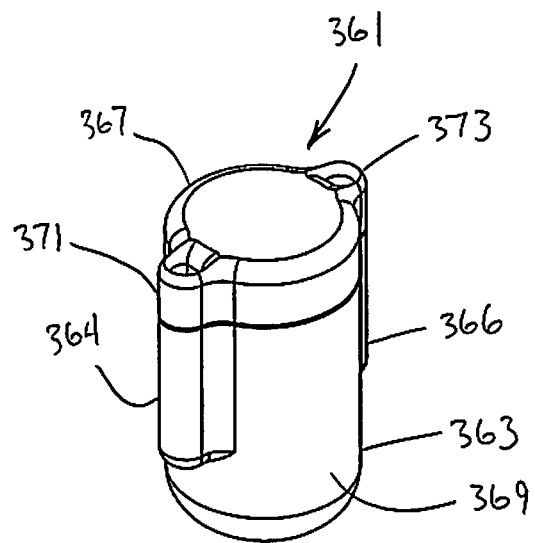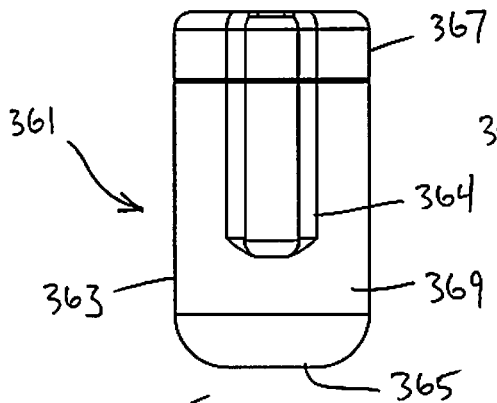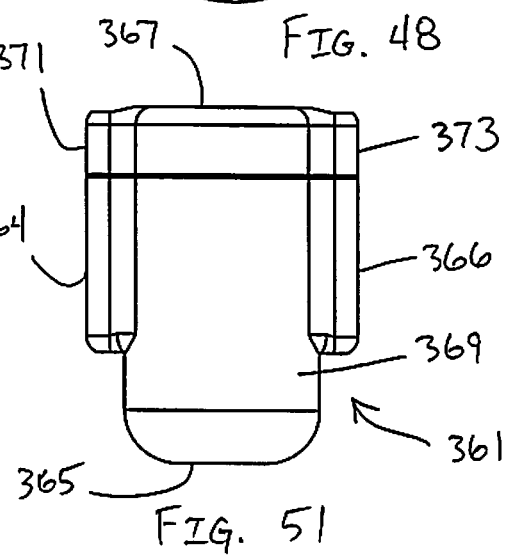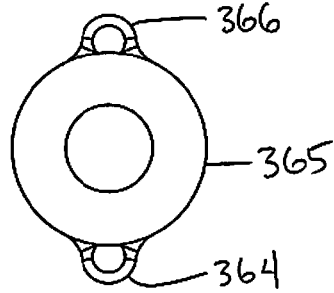

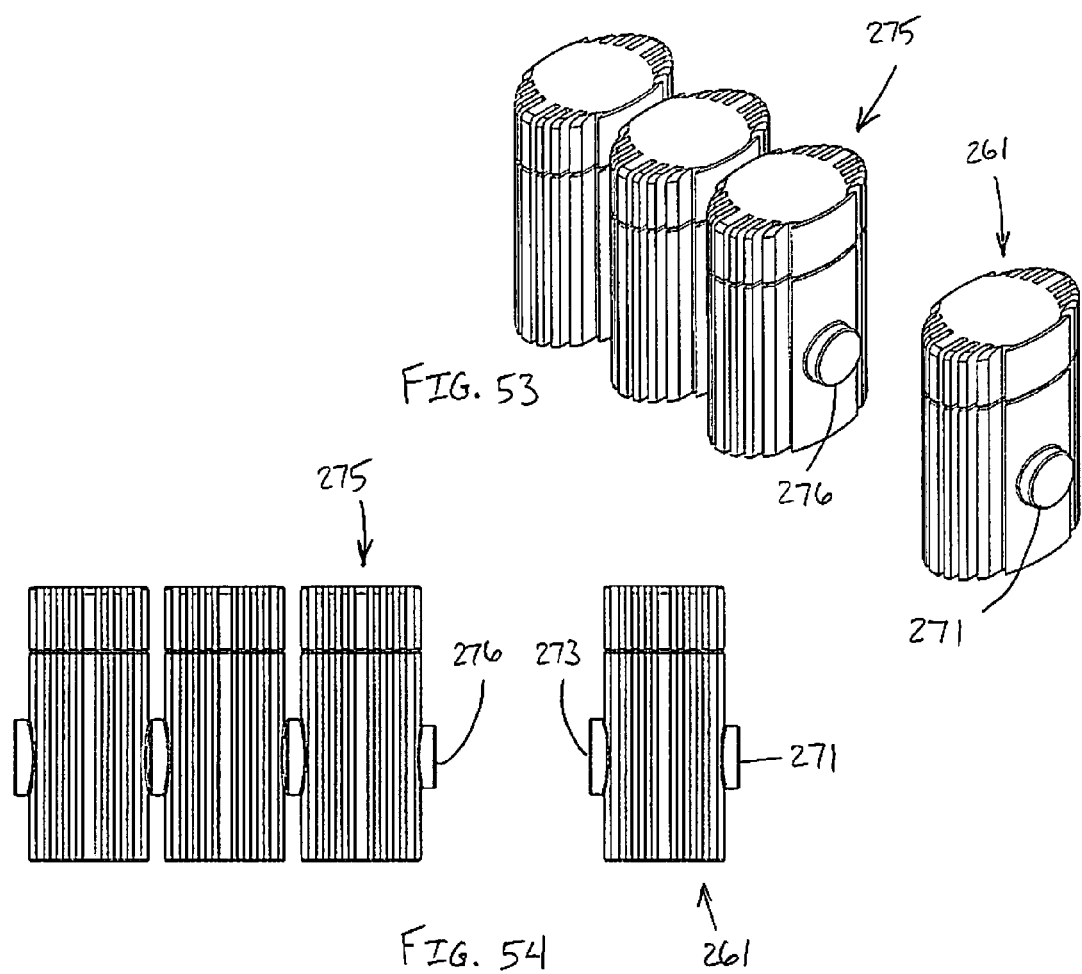

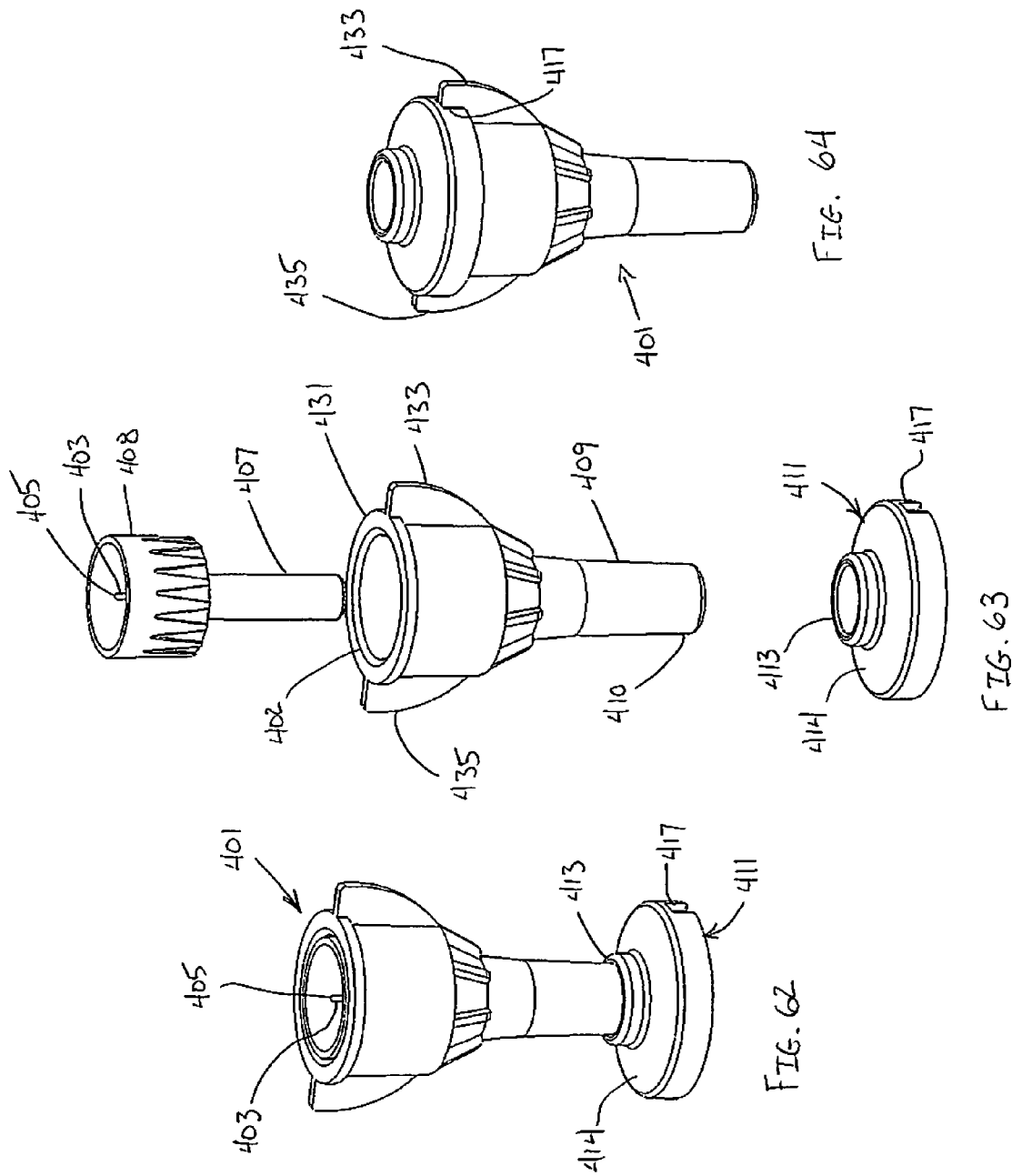

OUTER COVER OF A PEN NEEDLE FOR A DRUG DELIVERY PEN

RELATED APPLICATIONS

This application is a divisional of U.S. Ser. No. 12/563,092, filed on Sep. 18, 2009, which is hereby incorporated by reference in its entirety.

FIELD OF THE INVENTION

The present invention relates to a connecting member for removably connecting a plurality of pen needles to each other. The present invention further relates to an outer cover for a pen needle that facilitates connecting the pen needle to a drug delivery pen. The present invention still further relates to a cap for covering an outer cover of a pen needle.

BACKGROUND OF THE INVENTION

In certain circumstances, it is desirable to inject medication directly into human tissue. Typically, syringes or pen injection devices are used to inject medicaments into tissue areas, such as the intramuscular tissue layer, the subcutaneous tissue layer, and the intradermal tissue layer.

The assembly and operation of a typical pen injection device, as shown in FIGS. 1 and 2, is described in U.S. Patent Application Publication No. 2006/0229562, published on Oct. 12, 2006, which is hereby incorporated by reference in its entirety.

Pen injection devices, such as the exemplary pen injector 100, as shown in FIG. 1, typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is used by the user to securely hold the pen injector device 100 in a shirt pocket, purse or other suitable location.

FIG. 2 is an exploded view of an exemplary drug delivery pen shown in FIG. 1. The dose knob/button 24 has a dual purpose and is used to both set the dosage of the medication to be injected and to inject the dosed medicament via the lead screw 7 and stopper 15 through the medicament cartridge 12, which is attached to the drug delivery pen through a lower housing 17. In standard drug delivery pens, the dosing and delivery mechanisms are all found within the outer sleeve 13 and are not described in greater detail here as they are understood by those knowledgeable of the prior art. The distal movement of the plunger or stopper 15 within the medicament cartridge 12 causes medication to be forced into the needle 11 of the hub 20. The medicament cartridge 12 is sealed by septum 16, which is punctured by a septum penetrating needle cannula 18 located within the hub 20. The hub 20 is preferably screwed onto the lower housing 17, although other attachment means can be used such as attaching to the cartridge. To protect a user, or anyone who handles the pen injection device 100, an outer cover 69, which attaches to the hub 20, covers the hub. An inner shield 59 covers the patient needle 11 within the outer cover 69. The inner shield 59 can be secured to the hub 20 to cover the patient needle 11 by any suitable means, such as an interference fit or a snap fit. The outer cover 69 and inner shield 59 are removed prior to use. The cap 21 fits snugly against outer sleeve 13 to allow a user to securely carry the drug delivery pen 100.

The medicament cartridge 12 is typically a glass tube sealed at one end with the septum 16 and sealed at the other end with the stopper 15. The septum 16 is pierceable by a septum penetrating cannula 18 in the hub 20, but does not move with respect to the medicament cartridge 12. The stopper 15 is axially displaceable within the medicament cartridge 12 while maintaining a fluid tight seal.

A pen needle, which includes the hub 20, needle 11, outer shield 69 and inner shield 59, is typically used for a single injection and is then disposed of. Accordingly, patients must carry several pen needles to perform multiple injections over a period of time. Pen needles are generally stored loose in a container so that there is no simple and convenient way for a patient to keep multiple pen needles together. Accordingly, a need exists for removably connecting a plurality of pen needles together, thereby providing a patient with a convenient way to carry multiple pen needles.

Another problem a user encounters with drug delivery pens is difficulty in removing the packaging from the pen needle and attaching the pen needle to the drug delivery pen. Typically, a foil seal covers the non-patient needle end of the outer cover and must be removed prior to connecting the pen needle to the drug delivery pen. Additionally, the small size of the outer cover makes handling and connecting the pen needle difficult. Accordingly, a need exists for a pen needle that is easy to open and grip for the user.

Another problem encountered by a user is having to handle the outer cover while trying to put the outer cover back on the hub assembly, which can lead to an accidental needle stick. Furthermore, the non-injection end of the needle is left uncovered, which can also lead to an accidental needle stick. An additional need exists for a cap for an outer cover that encloses the non-injection end of the needle with a puncture-resistant cap.

Following an injection, the used needle, or "sharps", must be properly disposed of. Used sharps may become contaminated by body fluids and the like creating a hazard for anyone that may handle them following their use. Sharps disposal containers store the disposed sharps and prevent unintentional contact with any object disposed therein. Accordingly, a further need exists for an outer cover that completely encapsulates the pen needle within a puncture resistant cover and cap after use.

SUMMARY OF THE INVENTION

In accordance with an aspect of the present invention, a connecting member removably connects a plurality of pen needles together, thereby providing a convenient way for a patient to carry multiple pen needles.

In accordance with another aspect of the present invention, an outer cover of a pen needle has a shape and gripping members to facilitate handling by a user.

In accordance with yet another aspect of the present invention, a cap has a first opening for receiving a first end of an outer cover of a pen needle and a second opening for receiving a second end of the outer cover.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying figures, in which:

FIGS. 7-11 are perspective, top plan, side elevational, front elevational and bottom plan views, respectively, of an outer cover and lid according to another exemplary embodiment of the present invention;

FIGS. 12-15 are perspective, top plan, side elevational and bottom plan views, respectively, of an outer cover and lid according to another exemplary embodiment of the present invention;

FIGS. 16-19 are perspective, top plan, side elevational and bottom plan views, respectively, of an outer cover and lid according to another exemplary embodiment of the present invention;

FIGS. 20-25 are opposite side perspective, top plan, side elevational, front elevational and bottom plan views, respectively, of an outer cover and lid according to another exemplary embodiment of the present invention;

FIGS. 31-35 are perspective, top plan, side elevational, front elevational and bottom plan views, respectively, of an outer cover and lid according to another exemplary embodiment of the present invention;

FIGS. 36-41 are opposite side perspective, top plan, side elevational, front elevational and bottom plan views, respectively, of an outer cover and lid according to another exemplary embodiment of the present invention;

FIGS. 42-47 are opposite side perspective, top plan, side elevational, front elevational and bottom plan views, respectively, of an outer cover and lid according to another exemplary embodiment of the present invention;

FIGS. 48-52 are perspective, top plan, side elevational, front elevational and bottom plan views, respectively, of an outer cover and lid according to another exemplary embodiment of the present invention;

FIGS. 53 and 54 are perspective and side elevational views of the connectable outer cover of FIGS. 20-25 for a pen needle according to another exemplary embodiment of the present invention in which a plurality of outer covers are connected to each other;

FIG. 62 is a perspective view of the cap of FIG. 60 receiving a patient end of the pen needle outer cover;

FIG. 63 is an exploded perspective view of the cap and pen needle of FIG. 62; and FIG. 64 is a perspective view of the cap of FIG. 60 covering a non-patient end of the pen needle outer cover.

Throughout the drawings, like reference numbers will be understood to refer to like parts, components and structures.

DETAILED DESCRIPTION OF THE EXEMPLARY EMBODIMENTS

In an exemplary embodiment of the present invention, as shown in FIGS. 3-6, a connecting member removably connects a plurality of pen needles together, thereby providing a patient with a convenient way to carry multiple pen needles.

Figure 3:
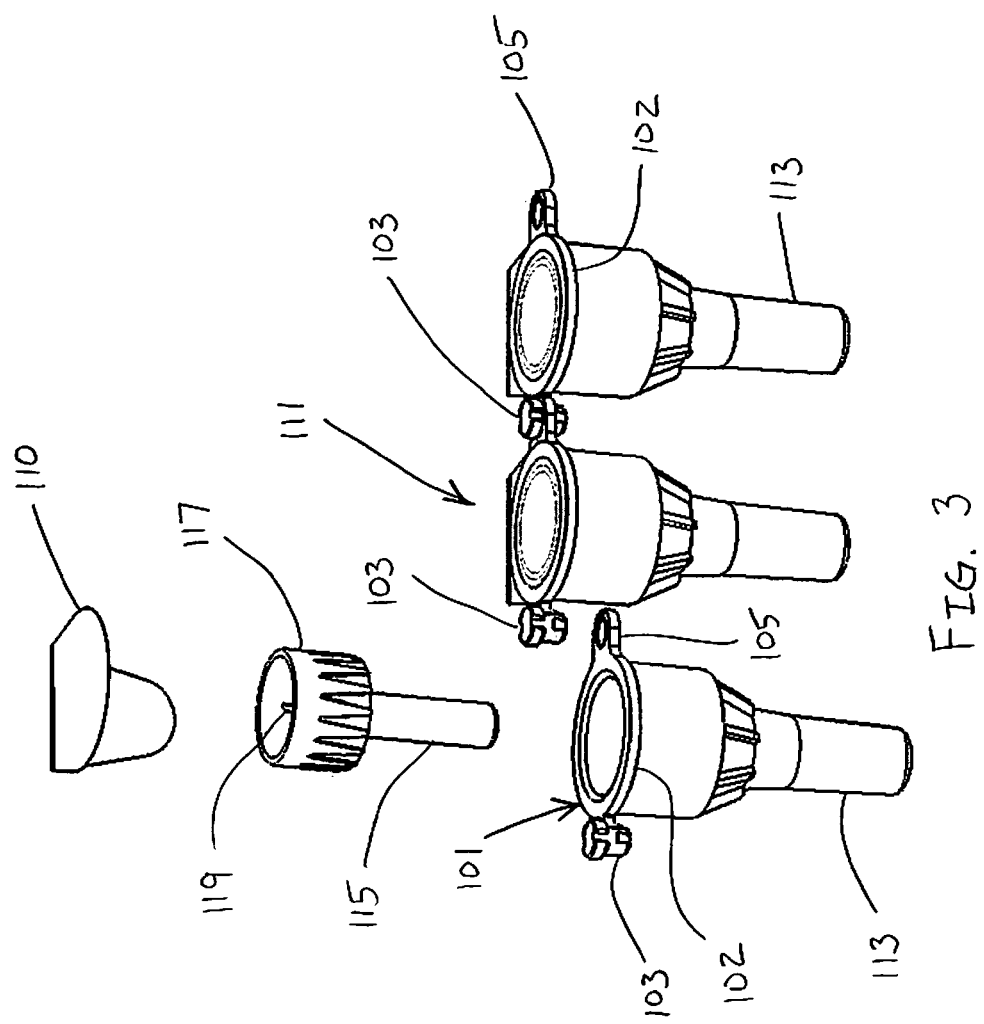
FIG. 3 is an exploded perspective view of an outer cover for a pen needle according to an exemplary embodiment of the present invention in which the outer covers are connectable.

As shown in FIG. 3, a connecting member 101 of a pen needle 111 includes a male member 103 and a female member 105. The pen needle 111 includes a hub 117 receiving a needle 119, an inner shield 115 connected to the hub and covering the patient end of the needle, and an outer cover 113 covering the inner shield and hub. A seal 110 covers the non-patient needle end of the hub 117.

Figure 1:
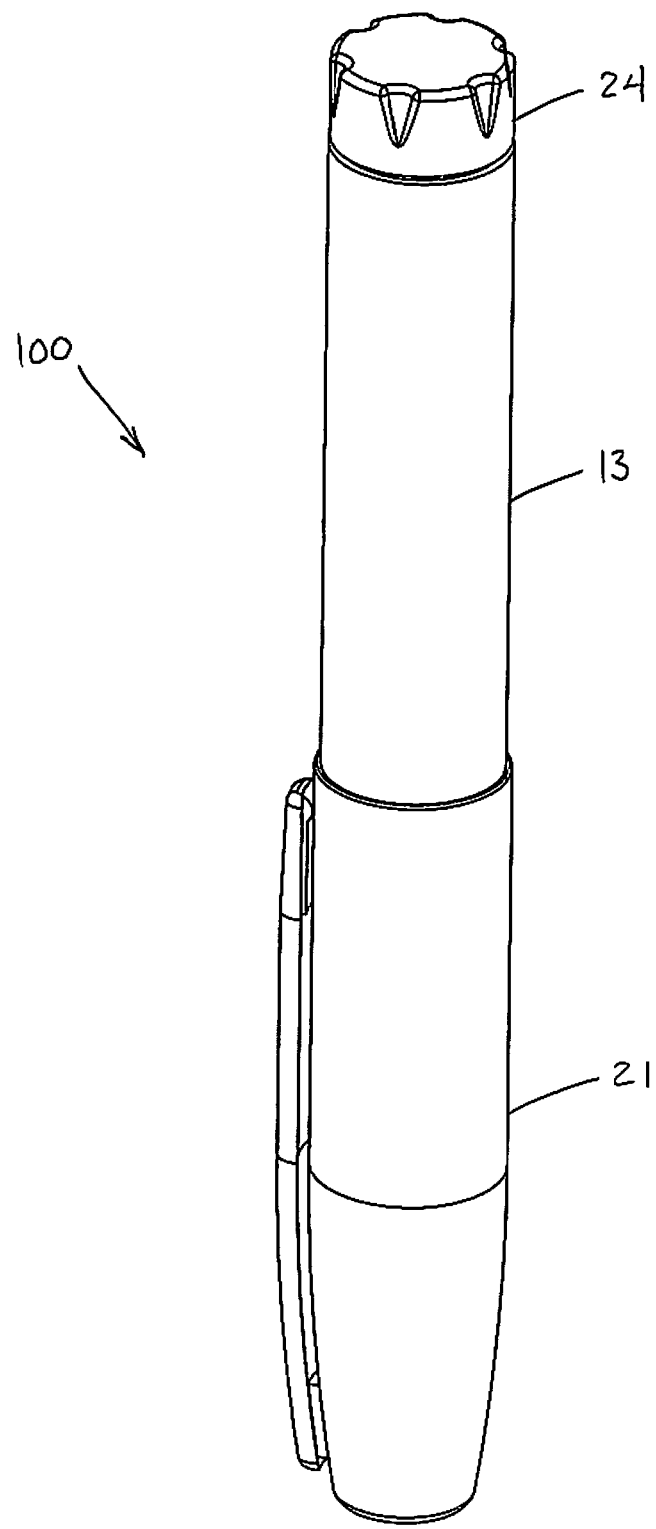
FIG. 1 is a perspective view of an assembled existing pen needle assembly.
Figure 2:
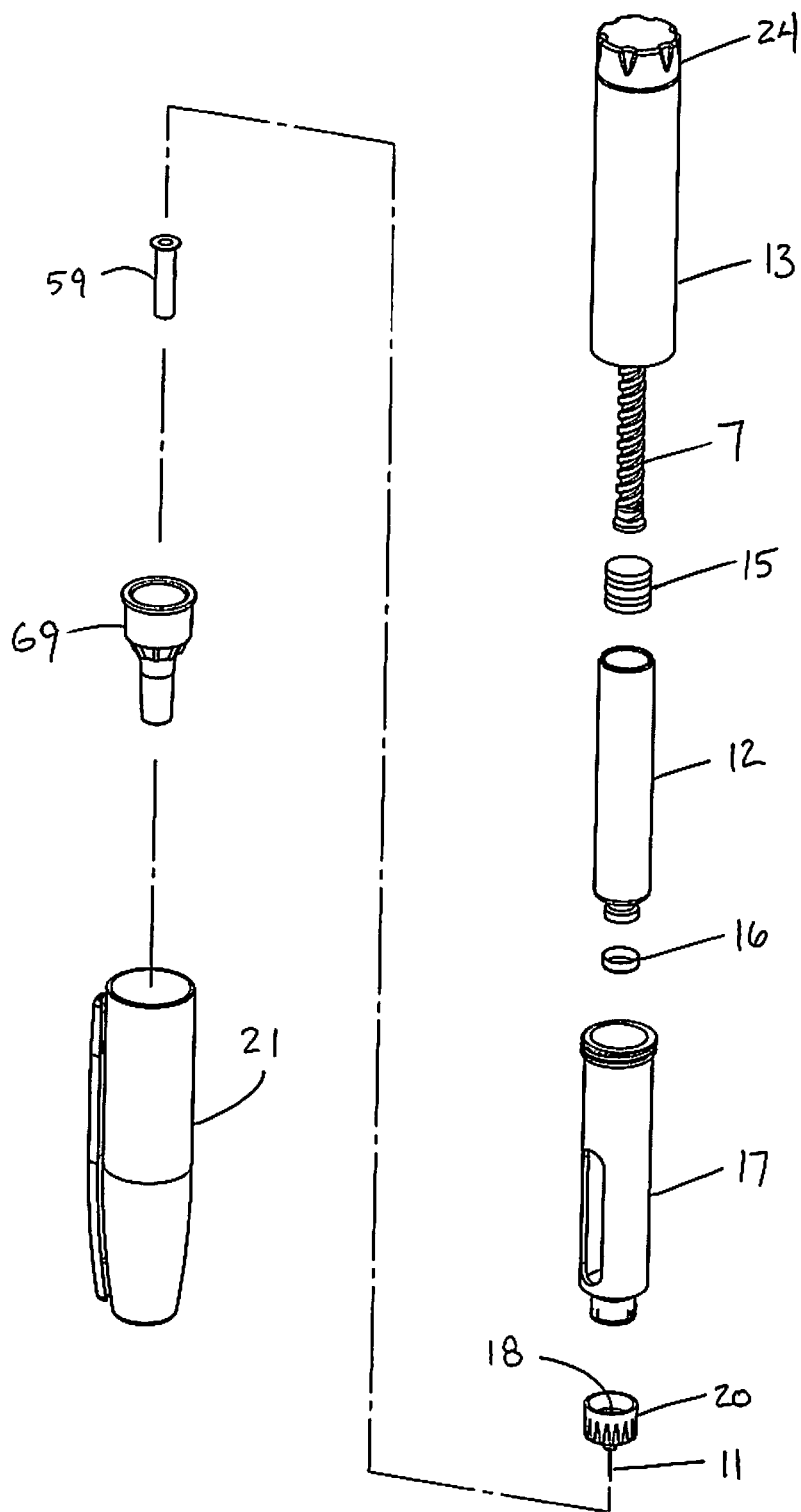
FIG. 2 is an exploded perspective view of the components of the pen needle assembly of FIG. 1.

A flange 102 is disposed at an end of the outer cover 113. A male member 103, such as a pin, is connected to the flange 102. A female member 105, such as a ring, is also connected to the flange 102. Preferably, the male and females members 103 and 105, respectively, are diametrically opposed on the flange 102. The male member 103 of a first pen needle 111 receives the female member 105 of a second pen needle 111, as shown in FIG. 3, such that a chain of pen needles can be formed. When an injection is to be made, the patient removes a pen needle at one end of the chain and connects the pen needle to the drug delivery pen 100 (FIGS. 1 and 2). Accordingly, a plurality of pen needles 111 may be removably connected together, thereby allowing a patient to easily carry multiple pen needles.

Figure 4:
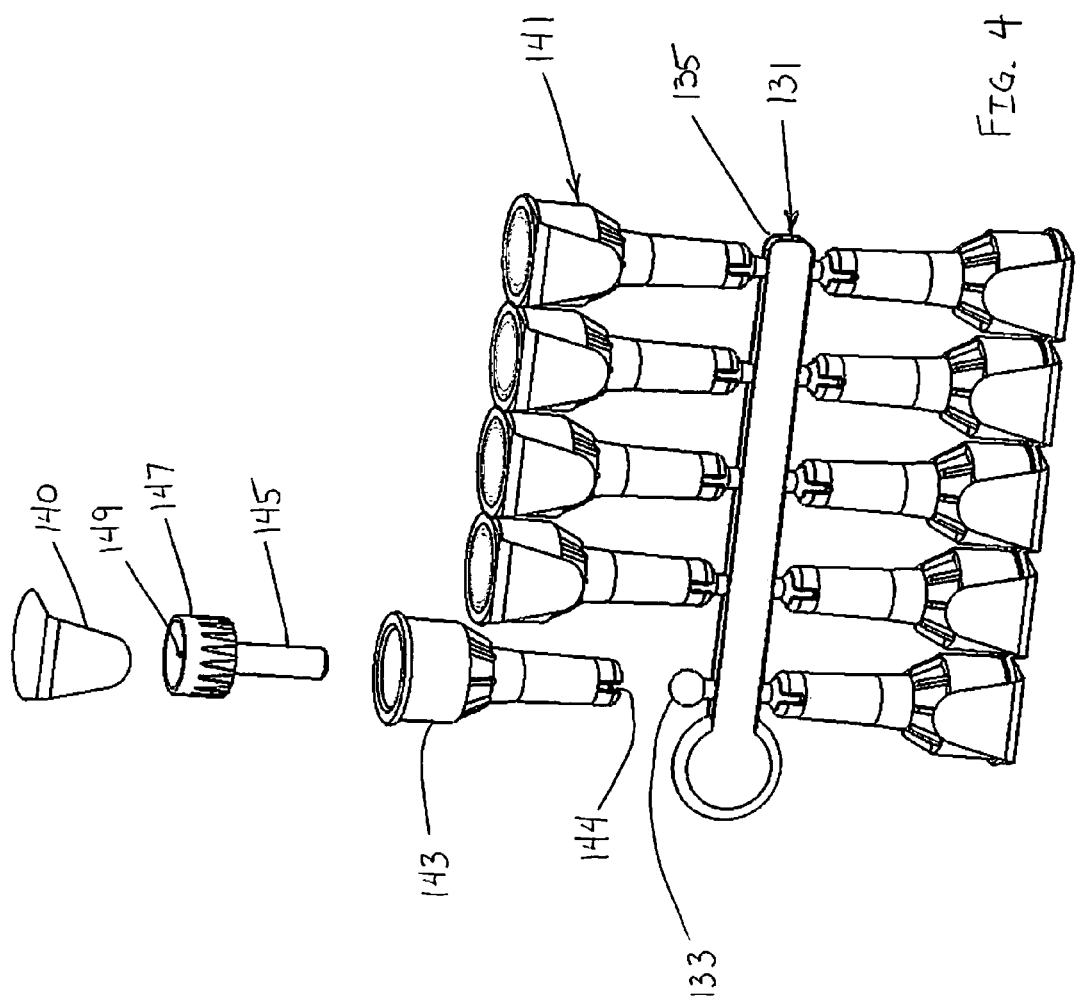
FIG. 4 is an exploded perspective view of a connecting member according to another exemplary embodiment of the present invention that receives a plurality of pen needles.

As shown in FIG. 4, a connecting member 131 removably receives a plurality of pen needles 141. The pen needle 141 includes a hub 147 receiving a needle 149, an inner shield 145 connected to the hub and covering the patient end of the needle, and an outer cover 143 covering the inner shield and hub. A seal 140 covers the non-patient needle end of the hub 147. An end of the outer cover 143 has a socket member 144 formed therein.

The connecting member 131 includes a spine 135 to which a plurality of ball members 133 are connected. Preferably, the ball members 133 are disposed on opposite sides of the spine 135. The connecting member 131 shown in FIG. 4 has a substantially linear spine 135. However, the connecting member may have any suitable shape, such as planar, spherical or circular. The ball member 133 removably receives the socket member 144 of the outer cover 143. When an injection is to be made, the patient removes a pen needle 141 from the connecting member 131 and connects the pen needle to the drug delivery pen 100 (FIGS. 1 and 2). Accordingly, the connecting member 131 removably receives a plurality of pen needles 141, thereby allowing a patient to easily carry multiple pen needles.

Figure 5:
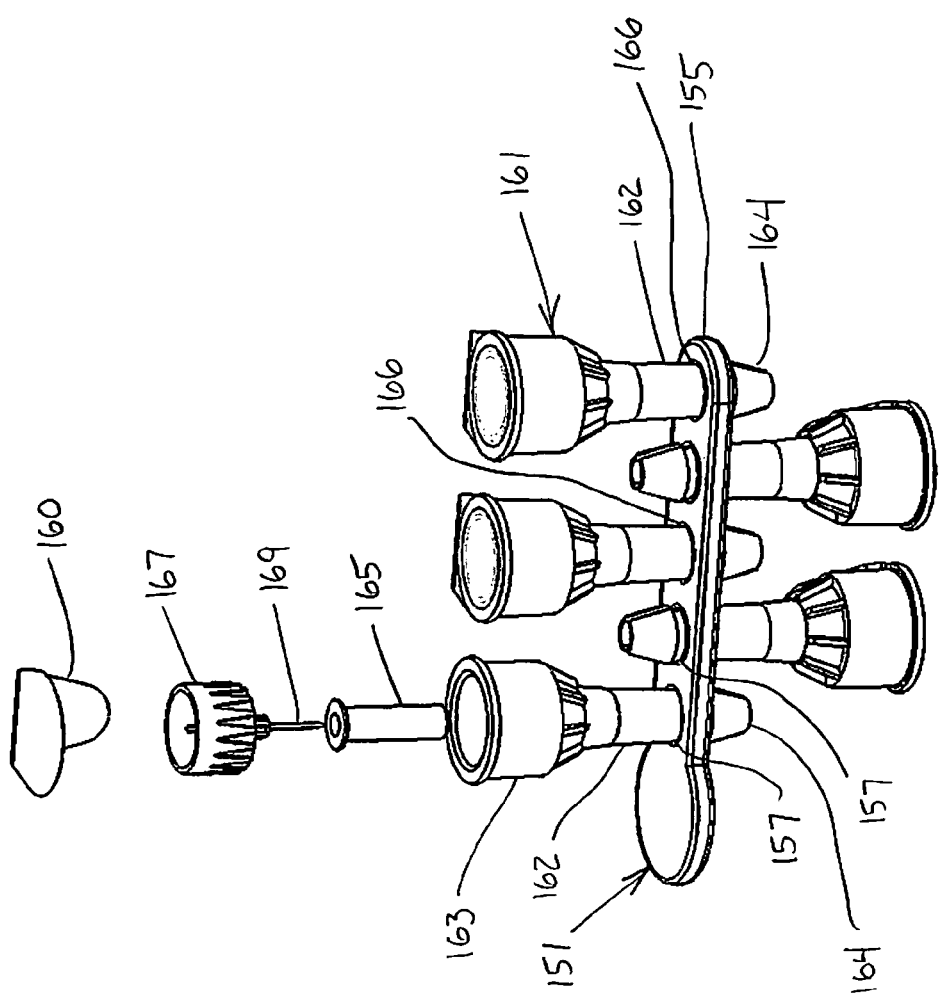
FIG. 5 is an exploded perspective view of a connecting member according to another exemplary embodiment of the present invention that receives a plurality of pen needles.

As shown in FIG. 5, a connecting member 151 removably receives a plurality of pen needles 161. The pen needle 161 includes a hub 167 receiving a needle 169, an inner shield 165 connected to the hub and covering the patient end of the needle, and an outer cover 163 covering the inner shield and hub. A seal 160 covers the non-patient needle end of the hub 167. A free end of a tubular portion 162 of the outer cover 163 has an enlarged head 164, and a groove 166 is formed in the tubular portion 162.

The connecting member 151 includes a spine 155 having a plurality of openings 157 formed therein. The connecting member 151 shown in FIG. 5 has a substantially linear spine 155. However, the connecting member may have any suitable shape, such as planar, spherical or circular. To connect a pen needle 161 to the connecting member 151, the enlarged head 164 of the outer cover 163 is passed through the opening 157 such that the groove 166 engages the opening 157. When an injection is to be made, the patient removes a pen needle 161 from the connecting member 151 and connects the pen needle to the drug delivery pen 100 (FIGS. 1 and 2). Accordingly, the connecting member 151 removably receives a plurality of pen needles 161, thereby allowing a patient to easily carry multiple pen needles.

Figure 6:
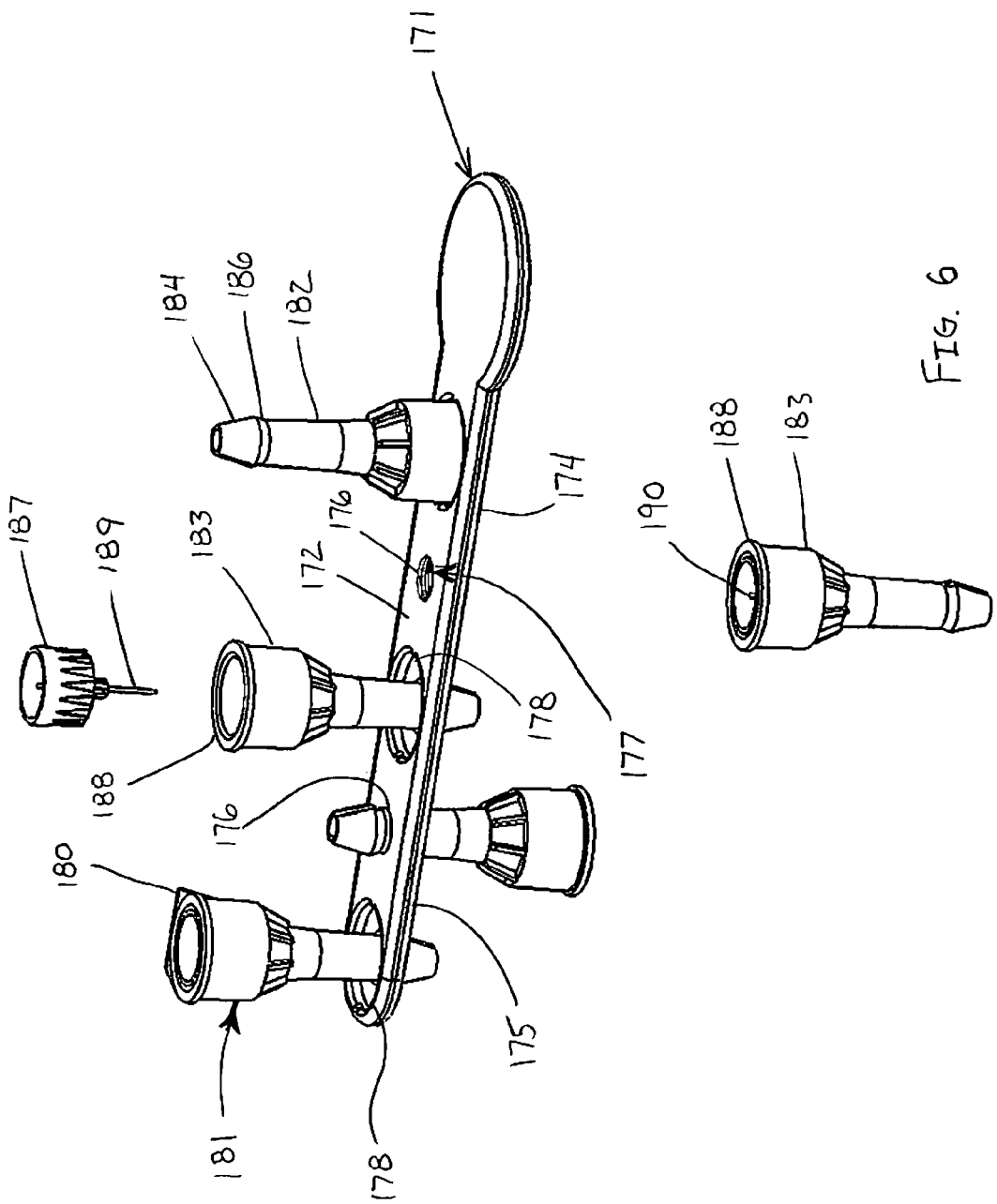
FIG. 6 is an exploded perspective view of a connecting member according to another exemplary embodiment of the present invention that receives a plurality of pen needles.
Figure 27:
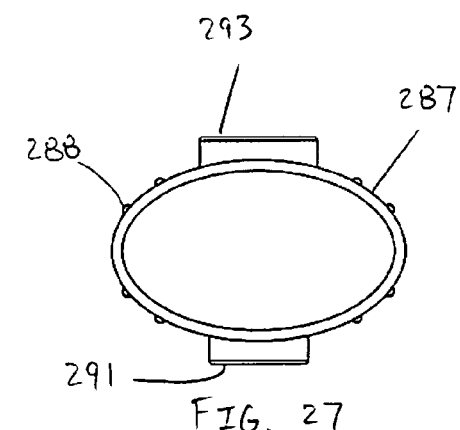
FIGS. 26-30 are perspective, top plan, front elevational, side elevational and bottom plan views, respectively, of an outer cover and lid according to another exemplary embodiment of the present invention.
Figure 26:
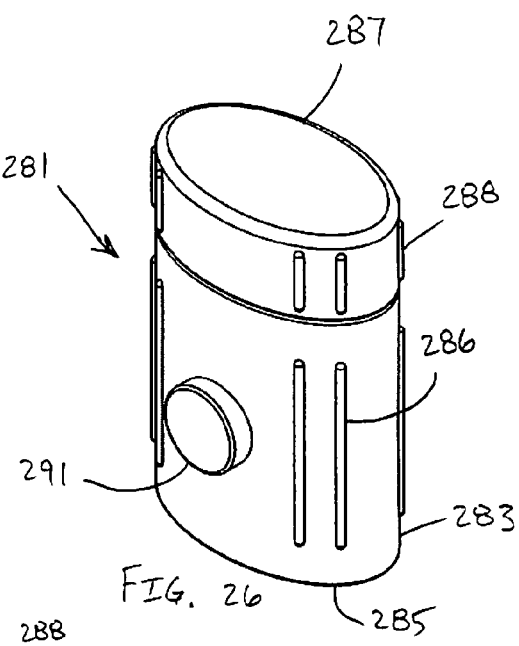
Figure 28:
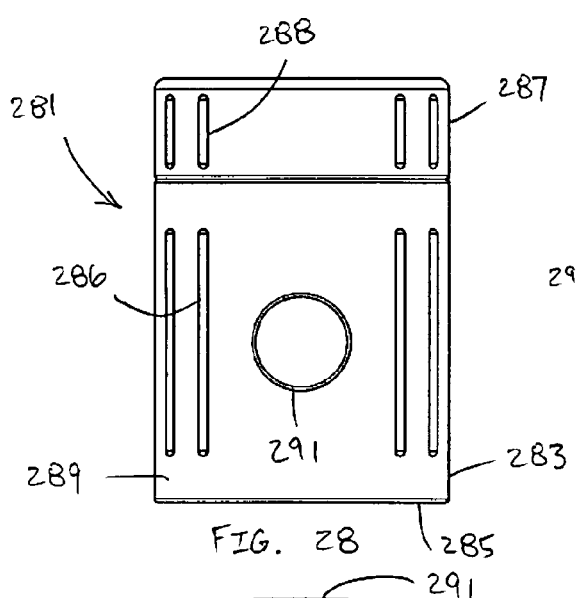
Figure 29:
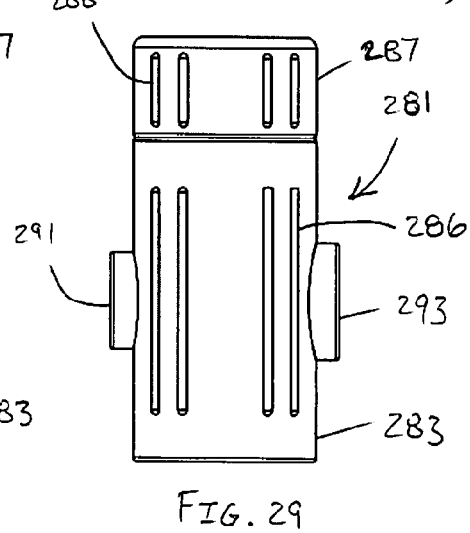
Figure 30:
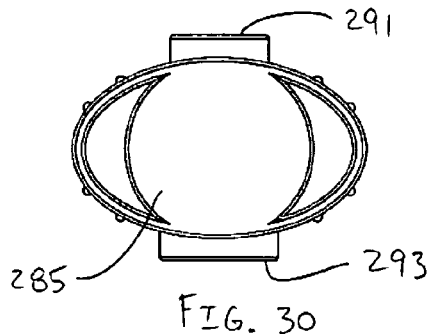
Figure 55:
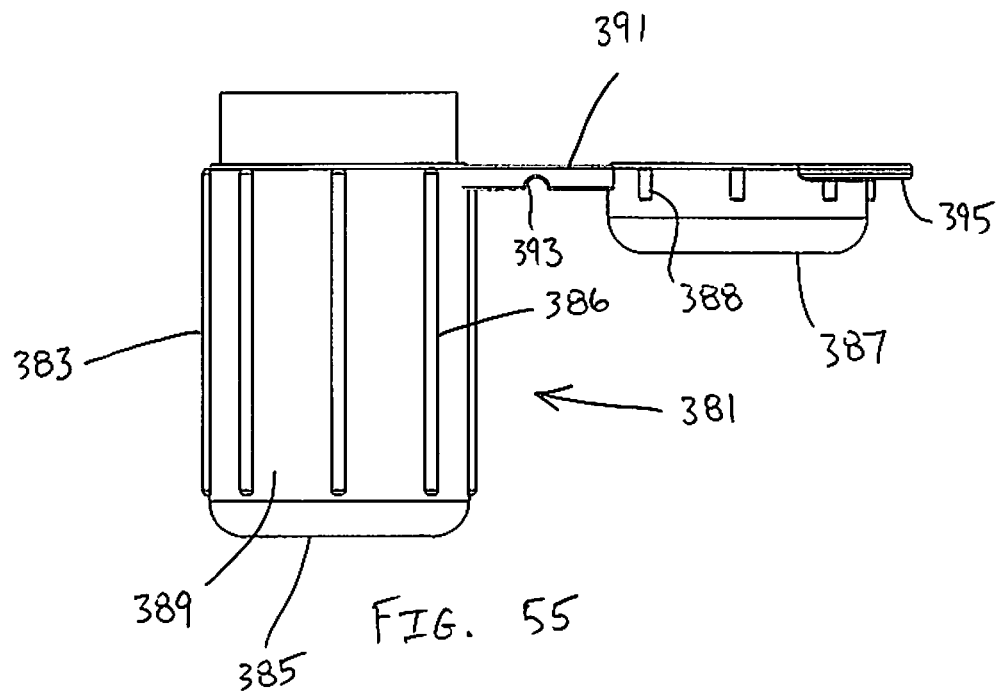
FIG. 55 is a side elevational view of an outer cover for a pen needle according to another exemplary embodiment of the present invention.
Figure 56:
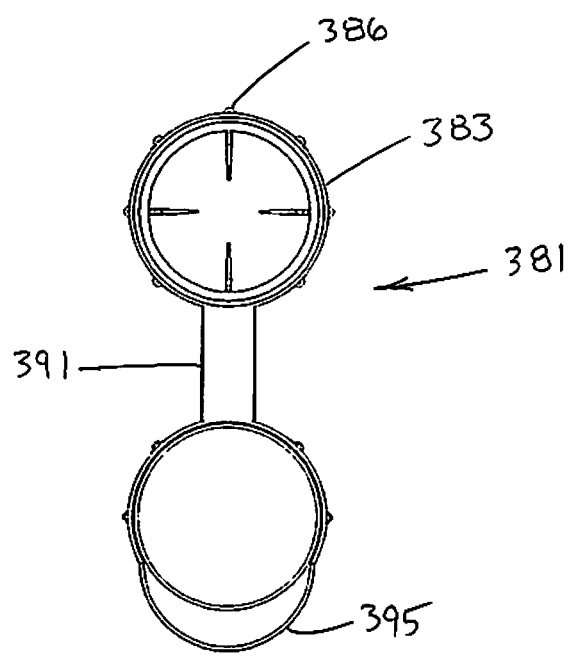
FIG. 56 is a top plan view of the outer cover of FIG. 55.
Figure 57:
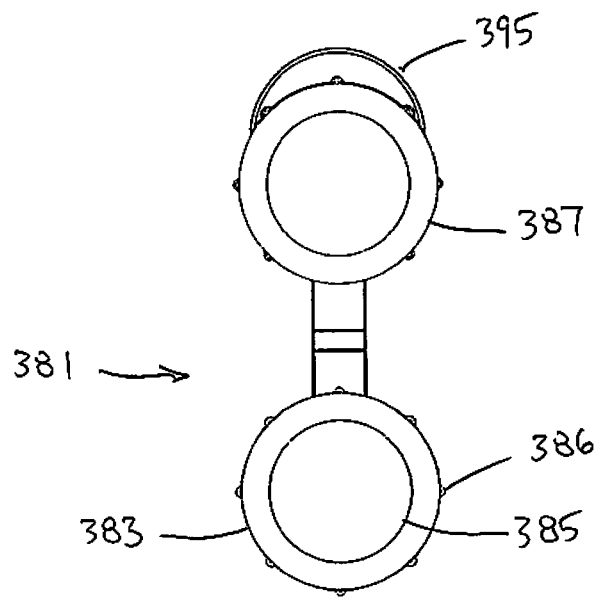
FIG. 57 is a bottom plan view of the outer cover of FIG. 55.
Figure 58:
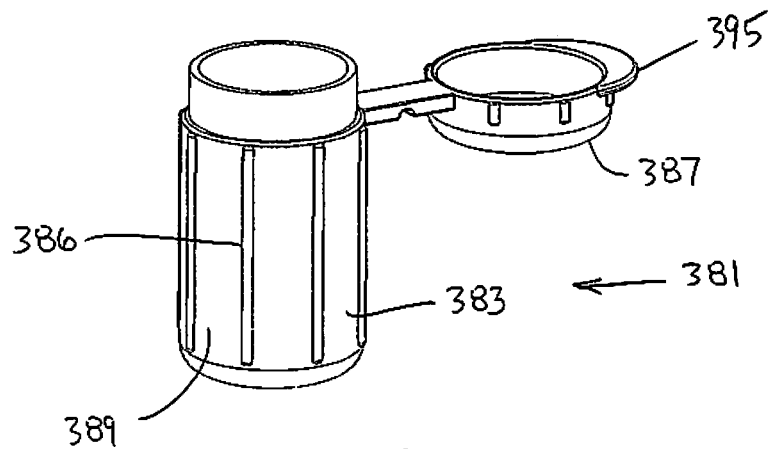
FIG. 58 is a perspective view of the outer cover of FIG. 55.

As shown in FIG. 6, a connecting member 171 removably receives a plurality of pen needles 181. The pen needle 181 includes a hub 187 receiving a needle 189, an inner shield (165 of FIG. 5) connected to the hub and covering the patient end of the needle, and an outer cover 183 covering the inner shield and hub. A seal 180 covers the non-patient needle end of the hub 187. A free end of a tubular portion 182 of the outer cover 183 has an enlarged head 184, and a groove 186 is formed in the tubular portion 182.

The connecting member 171 includes a spine 175 having a plurality of openings 177 formed therein. The opening 177 passes through from a first side 172 to a second side 174 of the spine 175. A first portion 176 of the opening 177 is adapted to receive the groove 186 of the outer cover 183. A second portion 178 of the opening 177 is disposed opposite the first portion 176 and is adapted to receive a flange 188 of the outer cover 183. The second portion 178 may retain the flange in any suitable manner, such as with tabs or an interference fit. Preferably, the first and second portions of the openings 177 are alternately disposed on each side of the spine 175.

Prior to use, the pen needle 181 is removably connected to the connecting member 171 such that the groove 186 is received by the first portion 176 of the opening 177. After the pen needle 181 has been used, the second portion 178 receives the flange 188 of the outer cover 183, thereby providing a cover to the non-patient end 190 of the needle 189. The connecting member 171 shown in FIG. 6 has a substantially linear spine 175. However, the connecting member may have any suitable shape, such as planar, spherical or circular.

To connect a pen needle 181 to the connecting member 171, the enlarged head 184 of the outer cover 183 is passed through the first portion 176 of the opening 177 such that the groove 186 engages the first portion 176 of the opening 177. When an injection is to be made, the patient removes a pen needle 181 from the connecting member 171, removes the seal 180 and connects the pen needle to the drug delivery pen 100 (FIGS. 1 and 2). After the injection has been made, the flange 188 of the outer cover 183 is connected to the second portion 178 of the opening 177 to secure the used pen needle to the connecting member 171 and cover the non-patient end 190 of the needle 189. Accordingly, the connecting member 171 removably receives a plurality of pen needles 181 both before and after use, thereby allowing a patient to easily carry multiple new and used pen needles.

Figure 59:
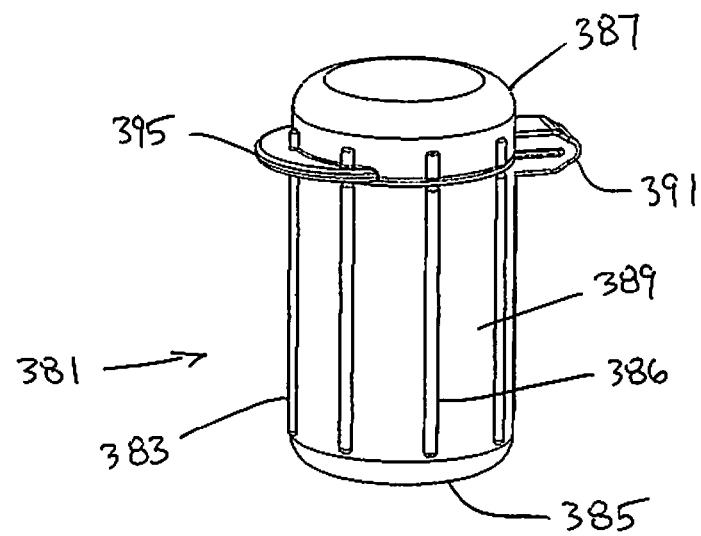
FIG. 59 is a perspective view of the outer cover of FIG. 55 in which the lid is closed.

Various configurations of outer covers and lids for pen needles are shown in FIGS. 7-59 that facilitate opening and gripping the pen needle. These outer covers and lids also function as a sharps container after the needle has been used. Accordingly, the hub assembly is completely encapsulated within a puncture resistant outer cover and lid. The outer covers shown in FIGS. 21-47, 53 and 54 allow the outer covers to be connected to one another, such that a user can carry multiple pen needles.

A first embodiment of a pen needle 201 is shown in FIGS. 7-11. An outer cover 203 receives the hub and needle (FIG. 2) therein. A plurality of ribs 206 extend axially along the outer surface 209 of the outer cover 203 to facilitate gripping the outer cover. The outer cover 203 has a substantially planar base 205 such that the pen needle 201 sits upright. A lid 207 is connected to an end of the outer cover 203 opposite the base 205. A disc-shaped handle 208 extends upwardly from the lid 207 to facilitate opening the pen needle 201 to access the hub and needle.

A second embodiment of a pen needle 221 is shown in FIGS. 12-15. An outer cover 223 receives the hub and needle (FIG. 2) therein. A first plurality of grooves 226 extend axially along the outer surface 229 of the outer cover 223 to facilitate gripping the outer cover. The outer cover 223 has a substantially planar base 225 such that the pen needle 221 sits upright. A lid 227 is connected to an end of the outer cover 223 opposite the base 225. A second plurality of grooves 228 extend along a tapered portion 231 of the lid 227 to facilitate gripping the lid to open the pen needle 221 to access the hub and needle. The lid 227 has a rounded top portion 233.

A third embodiment of a pen needle 241 is shown in FIGS. 16-19. An outer cover 243 receives the hub and needle (FIG. 2) therein. A first plurality of grooves 246 extend axially along an outer surface 249 of the outer cover 243 to facilitate gripping the outer cover. The outer cover 243 has a substantially planar base 245 such that the pen needle 241 sits upright. A lid 247 is connected to an end of the outer cover 243 opposite the base 245. A second plurality of grooves 248 extend along a tapered portion 251 of the lid 247 to facilitate gripping the lid to open the pen needle 241 to access the hub and needle. The lid 247 has a substantially planar top portion 253.

A fourth embodiment of a pen needle 261 is shown in FIGS. 20-25, 53 and 54. An outer cover 263 receives the hub and needle (FIG. 2) therein. A first plurality of ribs 266 extend axially along the outer surface 269 of the outer cover 263 to facilitate gripping the outer cover. The outer cover 263 has a substantially planar base 265 such that the pen needle 261 sits upright. A lid 267 is connected to an end of the outer cover 263 opposite the base 265. A second plurality of ribs 268 extend axially along the lid 267 to facilitate gripping the lid to open the pen needle 261 to access the hub and needle. In addition to facilitating a user's grip, the ribs provide a constant wall thickness for molding. A male connecting member 271 and a female connecting member 273 are disposed on opposite sides of the outer cover 263. A female member 273 of a first pen needle 261 is connectable to a male member 276 of a second pen needle 275, as shown in FIGS. 53 and 54, such that a plurality of pen needles can be connected together.

A fifth embodiment of a pen needle 281 is shown in FIGS. 26-30. An outer cover 283 receives the hub and needle (FIG. 2) therein. A first plurality of ribs 286 extend axially along the outer surface 289 of the outer cover 283 to facilitate gripping the outer cover. The outer cover 283 has a substantially planar base 285 such that the pen needle 281 sits upright. A lid 287 is connected to an end of the outer cover 283 opposite the base 285. A second plurality of ribs 288 extend axially along the lid 287 to facilitate gripping the lid to open the pen needle 281 to access the hub and needle. Preferably, the outer cover 283 and the lid 287 have a substantially oval shape to further enhance a user's grip thereon. A male connecting member 291 and a female connecting member 293 are disposed on opposite sides of the outer cover 283. A male member of a first outer cover is connectable to a female member of a second outer cover such that a plurality of pen needles can be connected together.

A sixth embodiment of a pen needle 301 is shown in FIGS. 31-35. An outer cover 303 receives the hub and needle (FIG. 2) therein. First and second ribs 304 and 306 extend axially along the outer surface 309 of the outer cover 303 to facilitate gripping the outer cover. The outer cover 303 has a substantially planar base 305 such that the pen needle 301 sits upright. A lid 307 is connected to an end of the outer cover 303 opposite the base 305. Third and fourth ribs 311 and 313 extend axially along the lid 307 to facilitate gripping the lid to open the pen needle 301 to access the hub and needle. A male connecting member 315 and a female connecting member 317 are disposed on opposite sides of the outer cover 303. A male member of a first outer cover is connectable to a female member of a second outer cover such that a plurality of pen needles can be connected together. The configuration shown in FIGS. 31-35 reduces the amount of plastic required to manufacture the outer cover 303 and lid 307.

A seventh embodiment of a pen needle 321 is shown in FIGS. 36-41. An outer cover 323 receives the hub and needle (FIG. 2) therein. A first plurality of ribs 326 extend axially along the outer surface 329 of the outer cover 323 to facilitate gripping the outer cover. The outer cover 323 has a substantially planar base 325 such that the pen needle 321 sits upright. A lid 327 is connected to an end of the outer cover 323 opposite the base 325. A second plurality of ribs 328 extend axially along the lid 327 to facilitate gripping the lid to open the pen needle 321 to access the hub and needle. A male connecting member 331 and a female connecting member 333 are disposed on opposite sides of the outer cover 323. A male member of a first outer cover is connectable to a female member of a second outer cover such that a plurality of pen needles can be connected together. The configuration shown in FIGS. 36-41 reduces the amount of plastic required to manufacture the outer cover 323 and lid 327.

An eighth embodiment of a pen needle 341 is shown in FIGS. 42-47. An outer cover 343 has two sections 345 and 347 for receiving two separate hub and needle assemblies (FIG. 2) therein. The first section 345 receives a first hub and needle, and a second section 347 receives a second hub and needle. The outer cover 343 is asymmetrical with a substantially oblong shape to facilitate gripping the outer cover. A first lid 349 is connected to the first section 345 of the outer cover 343. A second lid 351 is connected to the second section 347 of the outer cover opposite the first lid 349. A first plurality of ribs 350 extend axially along the first lid 349 to facilitate gripping the first lid to open the first section 345 of the pen needle 341 to access the hub and needle. A second plurality of ribs 352 extend axially along the second lid 351 to facilitate gripping the second lid to open the second section 347 of the pen needle 341 to access the hub and needle. A male connecting member 353 and a female connecting member 355 are disposed on opposite sides of the outer cover 343. A male member of a first outer cover is connectable to a female member of a second outer cover such that a plurality of pen needles can be connected together.

A ninth embodiment of a pen needle 361 is shown in FIGS. 48-52. An outer cover 363 receives the hub and needle (FIG. 2) therein. First and second ribs 364 and 366 extend axially along the outer surface 369 of the outer cover 363 to facilitate gripping the outer cover. The outer cover 363 has a substantially planar base 365 such that the pen needle 361 sits upright. A lid 367 is connected to an end of the outer cover 363 opposite the base 365. Third and fourth ribs 371 and 373 extend axially along the lid 367 to facilitate gripping the lid to open the pen needle 361 to access the hub and needle. The configuration shown in FIGS. 48-52 reduces the amount of plastic required to manufacture the outer cover 363 and lid 367. The reduction of the amount of plastic required for manufacturing is further facilitated by providing axial openings 375 through each of the ribs 364, 366, 371 and 373.

A tenth embodiment of a pen needle 381 is shown in FIGS. 55-59. An outer cover 383 receives the hub and needle (FIG. 2) therein. A first plurality of ribs 386 extend axially along the outer surface 389 of the outer cover 383 to facilitate gripping the outer cover. The outer cover 383 has a substantially planar base 385 such that the pen needle 381 sits upright. A lid 387 is connected to an end of the outer cover 383 opposite the base 385 by a flexible arm 391. The flexible arm 391 has a notch 393 therein to facilitate movement of the arm to move the lid 387 between an open position (FIG. 55) and a closed position (FIG. 59). Preferably, the outer cover 383, the lid 387 and the flexible arm 391 are integrally formed as one piece. A second plurality of ribs 388 extend axially along the lid 387 to facilitate gripping the lid to open the pen needle 381 to access the hub and needle. The lid 387 has a handle 395 extending outwardly therefrom to provide a gripping surface for a user to open and close the lid with respect to the outer cover 383.

A cap 411, as shown in FIGS. 60-64, covers a non-patient end 405 of the needle 403 of the pen needle 401 after the needle has been used for an injection. After injecting a medicament, an inner shield 407 may optionally be disposed over the patient end of the needle 403 to shield the needle and prevent any accidental needle sticks. The hub 408 and inner shield 407 are then disposed in an outer cover 409, as shown in FIGS. 62-64. The cap 411 is adapted to receive either the narrow end 410 of the outer cover 409 as shown in FIG. 62 or the flanged end 431 as shown in FIG. 64.

Figure 60:
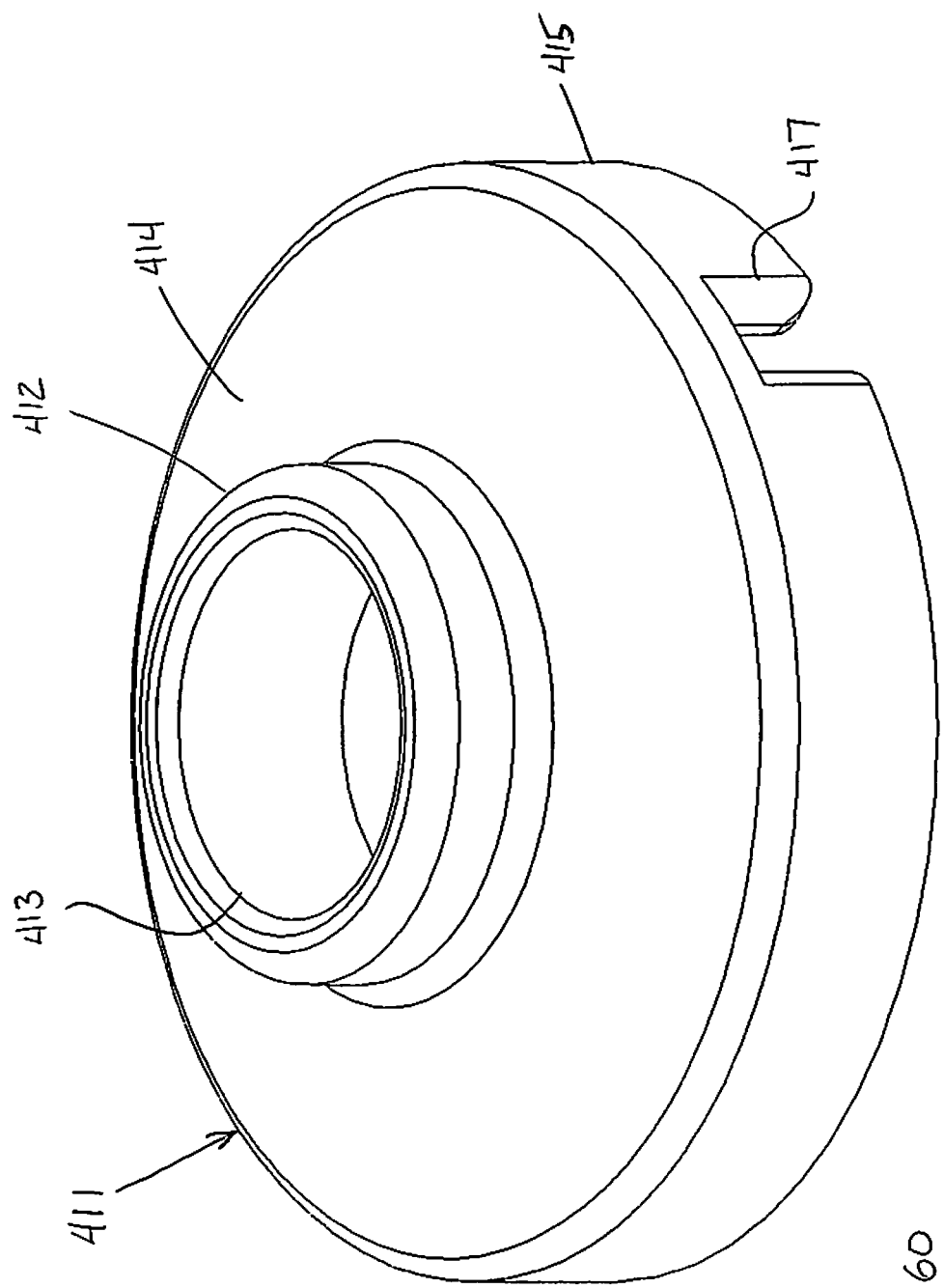
FIG. 60 is an upper perspective view of a cap for an outer cover of a pen needle according to another exemplary embodiment of the present invention.
Figure 61:
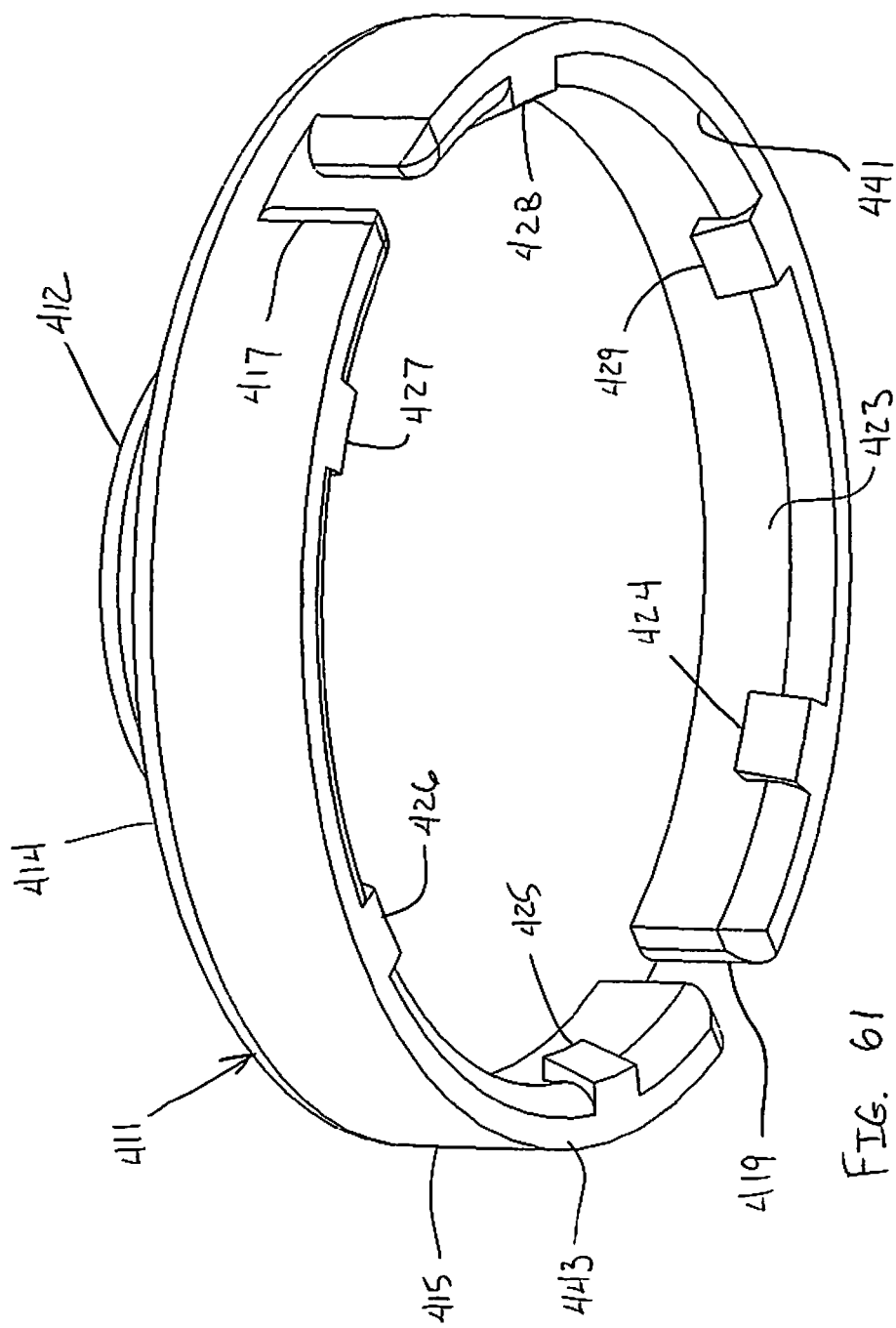
FIG. 61 is a lower perspective view of the cap of FIG. 60.

The cap 411, as shown in FIGS. 60 and 61, has a base 414 from which a projection 412 extends upwardly. A first opening 413 is formed in the projection that extends to the base 414. A side wall 415 extends downwardly from the base 414 and defines a second opening 441. The free end 443 of the side wall 415 is substantially planar, thereby allowing the cap 411 to rest flat on a planar surface. A pair of notches 417 and 419 are formed in the side wall 415 and are diametrically opposed from one another. Tabs 424-429 extend inwardly from an inner surface 423 of the side wall 415. Although six tabs are shown, any suitable number of tabs may be used.

Following an injection and after the inner shield 407 has been disposed on the needle 403, the cap 411 is placed on a planar surface. The narrow end 410 of the outer cover 409 is disposed in the first opening 413 in the projection 412 such that a friction fit is formed therebetween. A user can then reshield the hub 408 and inner shield 407 without holding the outer cover 409 by disposing the hub and inner shield in the opening 402 in the outer cover.

The reshielded pen needle 401 is then removed from the cap 411, and the cap is disposed on the flange 431 of the outer cover 409 such that the second opening 441 receives the flange 431 of the outer cover 409. The cap 411 is pushed downwardly on the outer cover 409 such that the flange moves over the tabs 424-429, thereby creating a snap fit between the cap 411 and the pen needle 401, as shown in FIG. 64, to securely lock the cap 411 to the pen needle 401. The notches 417 and 419 of the cap 411 receive the wings 433 and 435 of the outer cover 409. A tab or handle can be provided on the cap 411, such as handle 208 of FIG. 7, if the cap 411 is desired to be removable from the pen needle.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the invention as defined in the appended claims and their equivalents.

The invention claimed is:
1. A pen needle assembly, comprising:
 a plurality of pen needles, each having a hub, a needle connected to said hub, and an outer cover;
 each said outer cover having a tubular portion including a circular groove; and
 a connecting member having a plurality of openings for connecting said plurality of pen needles to each other, wherein
 each said groove engages one of said plurality of openings to connect the pen needle to the connecting member.
2. The pen needle assembly of claim 1, wherein
 said connecting member comprises a spine to which each of said plurality of pen needles is removably connected.
3. The pen needle assembly of claim 2, wherein
 said spine includes said plurality of openings adapted to removably receive said plurality of pen needles.
4. The pen needle assembly of claim 3, wherein
 a seal covers each said hub.
5. The pen needle assembly of claim 1, further comprising
 an inner shield connected to each said hub and covering a distal end of each said needle.
6. The pen needle assembly of claim 1, wherein
 each said outer cover includes an enlarged head adjacent to each said groove, and the enlarged head extends through the connecting member.

* * * * *